United States Patent
Maciá Barber et al.

(10) Patent No.: US 9,629,584 B2
(45) Date of Patent: Apr. 25, 2017

(54) SENSOR FOR ACQUIRING PHYSIOLOGICAL SIGNALS

(75) Inventors: Agustin Maciá Barber, Torrelodones (ES); Daniel Llorca Juan, Porto San Giorgio (IT)

(73) Assignee: SMART SOLUTIONS TECHNOLOGIES, S.L., Madrid (ES)

( * ) Notice: Subject to any disclaimer, the term of this patent is extended or adjusted under 35 U.S.C. 154(b) by 1014 days.

(21) Appl. No.: 13/988,007

(22) PCT Filed: Nov. 16, 2011

(86) PCT No.: PCT/EP2011/070296
§ 371 (c)(1),
(2), (4) Date: May 16, 2013

(87) PCT Pub. No.: WO2012/066056
PCT Pub. Date: May 24, 2012

(65) Prior Publication Data
US 2013/0225966 A1 Aug. 29, 2013

Related U.S. Application Data

(60) Provisional application No. 61/427,864, filed on Dec. 29, 2010.

(30) Foreign Application Priority Data

Nov. 17, 2010 (EP) .................................... 10191590

(51) Int. Cl.
A61B 5/0408 (2006.01)
A61B 5/00 (2006.01)

(52) U.S. Cl.
CPC ........ *A61B 5/6804* (2013.01); *A61B 5/04085* (2013.01); *A61B 2562/125* (2013.01)

(58) Field of Classification Search
CPC .............. A61B 5/6804; A61B 5/04085; A61B 2562/125
See application file for complete search history.

(56) References Cited

U.S. PATENT DOCUMENTS 3,954,100 A 5/1976 Sem-Jacobsen
3,993,049 A 11/1976 Kater
(Continued)

FOREIGN PATENT DOCUMENTS

CN 1732029 A 2/2006
EP 788811 A1 8/1997
(Continued)

OTHER PUBLICATIONS

I. Franta, Elastomers and Rubber Compounding Materials, Elsevier, 1989, p. 241.
(Continued)

*Primary Examiner* — Lee S Cohen
*Assistant Examiner* — Erin M Cardinal
(74) *Attorney, Agent, or Firm* — One3 IP Management, P.C.; Justin G. Sanders; Peter D. Weinstein

(57) ABSTRACT

The present invention relates to a sensor 1 for acquiring physiological signals with improved silicone rubber in particular when the sensor 1 is included in a garment 7 and the person who wears the garment 7 is in high level activity, the invention furthermore relates to a device comprising the sensor, as well as garments 7 comprising the device.

19 Claims, 12 Drawing Sheets

(56) References Cited

U.S. PATENT DOCUMENTS

| | | | |
|---|---|---|---|
| 4,082,087 A | 4/1978 | Howson | |
| 4,664,118 A | 5/1987 | Batters | |
| 4,867,166 A | 9/1989 | Axelgaard et al. | |
| 4,941,961 A | 7/1990 | Noguchi et al. | |
| 5,164,443 A | 11/1992 | Watanabe | |
| 5,289,822 A | 3/1994 | Highe | |
| 5,352,315 A | 10/1994 | Carrier et al. | |
| 5,427,096 A | 6/1995 | Bogusiewicz et al. | |
| 5,746,207 A | 5/1998 | McLaughlin et al. | |
| 5,947,897 A | 9/1999 | Otake | |
| 6,270,466 B1 | 8/2001 | Weinstein et al. | |
| 6,419,636 B1* | 7/2002 | Young | A61B 5/015 600/372 |
| 6,745,082 B2 | 6/2004 | Axelgaard | |
| 7,173,437 B2 | 2/2007 | Hervieux et al. | |
| 7,324,841 B2 | 1/2008 | Reho et al. | |
| 7,502,643 B2 | 3/2009 | Farringdon et al. | |
| 7,522,951 B2 | 4/2009 | Gough et al. | |
| 7,779,656 B2 | 8/2010 | Dias et al. | |
| 7,783,334 B2 | 8/2010 | Nam et al. | |
| 8,112,140 B2 | 2/2012 | Grabetal | |
| 8,369,936 B2 | 2/2013 | Farringdon et al. | |
| 8,700,118 B2 | 4/2014 | Oster et al. | |
| 8,818,478 B2 | 8/2014 | Scheffler et al. | |
| 2003/0163035 A1* | 8/2003 | Van Heerden | A61N 1/0492 600/397 |
| 2005/0177059 A1 | 8/2005 | Koivumaa et al. | |
| 2006/0094948 A1 | 5/2006 | Gough et al. | |
| 2006/0095001 A1 | 5/2006 | Matsumura et al. | |
| 2006/0183990 A1* | 8/2006 | Tolvanen | A61B 5/6805 600/386 |
| 2007/0060859 A1 | 3/2007 | Kanamura et al. | |
| 2007/0127187 A1* | 6/2007 | DeFusco | A61B 5/0245 361/220 |
| 2008/0242176 A1 | 10/2008 | Jaeger et al. | |
| 2008/0287769 A1 | 11/2008 | Kurzweil et al. | |
| 2009/0043185 A1 | 2/2009 | McAdams et al. | |
| 2009/0100566 A1 | 4/2009 | Schiavino et al. | |
| 2009/0282671 A1 | 11/2009 | Tao et al. | |
| 2010/0070007 A1 | 3/2010 | Parker et al. | |
| 2010/0185076 A1* | 7/2010 | Jeong | A61B 5/0408 600/388 |
| 2010/0198038 A1 | 8/2010 | Nagata et al. | |
| 2010/0198043 A1 | 8/2010 | Holzer et al. | |
| 2010/0234715 A1 | 9/2010 | Shin et al. | |
| 2011/0230749 A1* | 9/2011 | Chan | A61B 5/0408 600/393 |
| 2011/0259638 A1* | 10/2011 | Sherrill | A61B 5/04085 174/70 R |
| 2012/0246795 A1 | 10/2012 | Scheffler et al. | |
| 2013/0225966 A1 | 8/2013 | Barber et al. | |
| 2013/0338472 A1 | 12/2013 | Barber et al. | |

FOREIGN PATENT DOCUMENTS

| | | |
|---|---|---|
| EP | 1361819 B1 | 11/2003 |
| EP | 2072009 A1 | 6/2009 |
| EP | 2196142 A1 | 6/2010 |
| JP | S55-108455 A | 8/1980 |
| JP | 2001-234070 A | 8/2001 |
| RU | 2237303 C2 | 9/2004 |
| RU | 55241 U1 | 7/2006 |
| WO | 9718450 A1 | 5/1997 |
| WO | 0102052 A2 | 11/2001 |
| WO | 0230279 A1 | 4/2002 |
| WO | 0239894 A1 | 5/2002 |
| WO | 02071935 A1 | 9/2002 |
| WO | 2004058346 A1 | 7/2004 |
| WO | 2004110192 A1 | 12/2004 |
| WO | 2005088772 A1 | 9/2005 |
| WO | 2006101748 A3 | 9/2006 |
| WO | 2007050650 A2 | 5/2007 |
| WO | 2009020274 A1 | 2/2009 |

OTHER PUBLICATIONS

Search Report, The State Intellectual Property Office of the People's Republic of China, dated Oct. 20, 2015.

Anjum, et al., Fabrication of Extrinsically Conductive Silicone Rubbers with High Elasticity and Analysis of Their Mechanical and Electrical Characteristics, Polymers 2(3): 200-210 (2010).

Carpi & De Rossi, Electroactive Polymer-Based Devices for e-Textiles in Biomedicine, IEEE Transactions on Information Technology in Biomedicine 9(3): 295-318 (2005).

De Rossi & Veltink, Wearable Technology for Biomechanics: e-Textile or Micromechanical Sensors?, IEEE Engineering in Medicine and Biology Magazine, 29: 37-43 (2010).

Mecking, EPO European Search Report for EP 2010191590.8, (Apr. 28, 2011).

Mecking, PCT International Search Report & Written Opinion, PCT/EP2011/070296, pp. 11 (Jun. 2, 2012).

Medeiros, PCT International Search Report & Written Opinion, PCT/EP2012/056573, pp. 23 (Mar. 25, 2013).

Moller, EPO Extended European Search Report for EP 2012174367.8, (Oct. 1, 2012).

* cited by examiner

SENSOR FOR ACQUIRING PHYSIOLOGICAL SIGNALS

This patent application is a U.S. national phase filing under 35 U.S.C. §371 from International Patent Application PCT/EP2011/070296, filed Nov. 16, 2011 which claims priority pursuant to 35 U.S.C. §119(e) to U.S. Provisional Patent Application 61/427,864, filed Dec. 29, 2010, and which claims priority pursuant to 35 U.S.C. §119(d) to EP. Patent Application 10191590.8, filed Nov. 17, 2010, each of which is hereby incorporated by reference in its entirety.

The present invention relates to sensors for acquiring physiological signals, devices comprising these sensors, as well as garments comprising these devices.

BACKGROUND ART

Sensors comprising electrodes are used extensively in the assessment of clinical condition, for example in the monitoring of cardiac condition. The electrodes are placed in contact with the skin of the human body and the electrical physiological signals which result are examined.

Nevertheless, stability, noise and sensibility of the signals can be affected by different reasons; motion and long term acquisition of the signal are two of the most significant.

One of the physiological signals most affected by the different types of noise, as electrode contact noise or movement noise is the Electrocardiogram (ECG) signals. ECG is a long term analysis and to acquire a good signal it is crucial that the signal's parameters are stables.

As the ECG is a long term analysis, a garment that include an ECG sensor is essential to monitor this type of physiological signals in the daily live.

It is known in the state of the art, garments with sensors integrated in the textile. The sensor to be integrated in a garment must be a system minimal invasive, flexible, conformable to the human body including in movement, comfortable and resistant to repeated washing.

The current state of the art in textile sensors presents different drawbacks:

i) Low adhesion to skin. Each relative motion between skin and electrode causes alterations in the signal. This limitation is very significant in the context of use of electrodes during physical activity.

ii) Signal alterations. These are produced by the movement of the conductive fibers and the presence of wrinkles.

iii) Decrease of the signal quality with time. In some sensors to ensure the skin contact, liquids such as water or grease can be used between the contact layer and the skin. In dry environments it is not possible to remain the skin moisture level constant and the electric conductivity of the contact layer decreases.

The patent application EP1361819, which applicant was Polar Electro, OY., describes a sensor which comprises a contact layer including conductive fibers, and a moisture layer for retaining moisture on the top of the contact layer. The moisture layer retains secretory products from the skin, such as moisture and electrolytes. This enhances the contact between the skin and the contact layer and increases the electric conductivity of the contact layer, but the comfortable of the garment is minor as the humidity in the skin and inside the garment is increased.

The patent application EP2072009 describes a garment comprising at least one electrocardiogram sensor integrated into the garment comprising an electrode on the inside of the garment and arranged to contact a user's skin; and a resilient compressible filler provided between the garment and the electrode. The resilient compressible filler holds the electrode in place when the garment moves. The resilient compressible filler could be uncomfortable for the user.

The patent application US20100234715 describes a garment for measuring physiological signals. The garment including an electrode sensor coupled to an inner surface of a garment to make contact with the skin for detecting physiological signals; a signal connection line connected to the electrode sensor, a snap and a measurement unit. The electrode sensor unit is coupled to a desired portion of a garment using a coupling adhesive member which is may have opened frame shape for attaching edges of the electrode sensor to the garment. An anti slipping adhesive tape (member) may be formed along the border of the electrode sensor and the coupling adhesive member.

Thus, from what is known in the art, it is derived that the development of a sensor and a garment comprising the sensor which allow recording physiological signals, especially in movement, with improved adhesion properties but avoiding adhesive elements which produce skin irritations and with flexibility properties, is still of great interest.

SUMMARY OF THE INVENTION

Inventors have found a sensor 1 with improved anti-slip property, in particular when the sensor 1 is included in a garment 7 and the person who wears the garment 7 is in high level of activity as occurred, for instance, during sport practice. The sensor 1 shows excellent flexibility properties.

The sensor 1 comprises a conductive layer 2 comprising a plurality of orificies 6 or grooves 11 in a predefined pattern, filled with silicone rubber. The silicone rubber avoids the use of adhesive materials to fix the sensor 1 to the skin 12 which is advantageous since these adhesive materials, in long term acquisition of signals, could irritate the skin, and they loose their adhesive properties with repeating washing. The sensor 1 also comprises an electrical connector 5.

The conductive layer 2 of the invention contains metal, usually this kind of layer is not flexible, but the orifices 6 or grooves 11 on the conductive layer 2 improve the flexibility and improve the adaptation conductive layer/body shape.

The fact that the sensor 1 of the present invention shows excellent anti-slip and flexibility properties is advantageous for receiving physiological signals with the required quality and for a long time. Besides, the good contact sensor-skin and the excellent fixation reduce the noise of the signal.

In some physiological signals, as the ECG, noise can make measurement of the signal very difficult. The quality of ECG sensors can have a significant impact on the acquisition of the signal. The quality depends on the electrode electrical properties and the contact stability electrode/skin. The more quality and stability the signal has, the more easily the doctor can discern between pathologies and the more reliability can be given in a diagnosis of the patient. ECG signals recorded with smart clothes in case of high level activity show disturbances as intermittent loss of signals from electrodes.

Nothing in the art suggests that a sensor with a conductive layer comprising a plurality of orifices filled with silicone rubber could confer excellent fixation and flexibility properties.

Therefore, an aspect of the present invention relates to a sensor 1 to be placed in contact with the skin 12 of an user for acquiring physiological signals which comprises: a) a conductive layer 2 comprising at least conductive fibers to be placed in contact with the skin 12 for receiving physiological signals; b) an electrical connector 5 connected to the conductive layer 2; characterized in that the conductive layer 2 comprises a plurality of orifices 6 filled with an silicone rubber throughout the conductive area.

The sensor 1 is capable to detecting electrical physiological signals of the user.

Another aspect of the invention relates to a device comprising at least one sensor 1 of the invention and an electronic instrument 14 for receiving and collecting and/or storing and/or processing, and/or transmitting data from said sensor 1.

The present invention provides a sensor 1 adapted to be integrated in a garment 7 so as to be placed in contact with skin 12 of a user during the use of the garment 7. Therefore, another aspect of the invention relates to a garment 7 comprising at least the device of the invention.

Also, it is provided a preparation process of the sensor 1, which comprises the steps of:
a) die cutting a conductive layer of conductive fabric;
b) adding a hot melt adhesive on one surface of the conductive layer;
c) screen printing with an anti-slip silicone rubber on the the orifices 6 or grooves 11 of the electrode 3; and
d) curing the silicone;
wherein the step a), b) can be carried out in any order.

DETAILED DESCRIPTION OF THE INVENTION

Figure 1A:
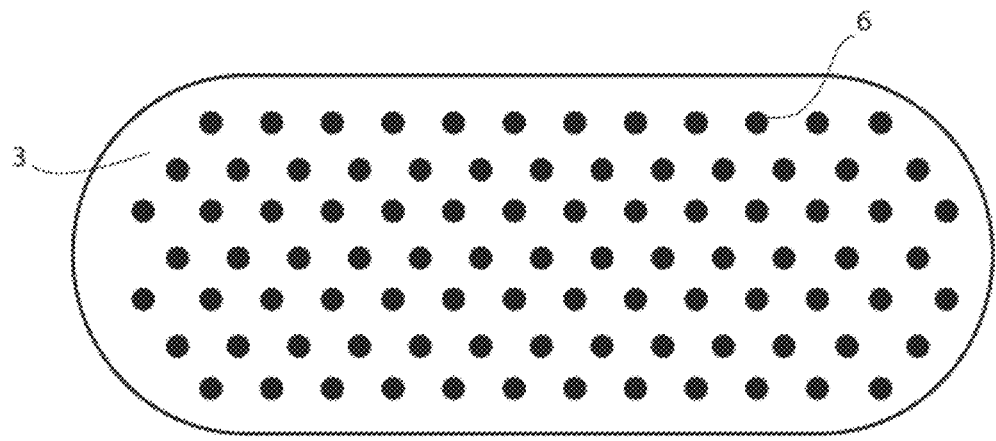
FIG. 1A illustrates an orifices 6 pattern in the electrode 3.

A target of the present invention is the monitoring of the user in physical activity on a continuous and non-invasive mode, without adding any restrictions. Thus, the sensor 1 of the present invention allows measuring the electrical physiological signals during physical activity.

As mentioned above, a first aspect of the invention relates to a sensor 1 to be placed in contact with the skin 12 of an user for acquiring physiological signals which comprises:a) a conductive layer 2 comprising at least conductive fibers to be placed in contact with the skin 12 for receiving physiological signals;b) an electrical connector 5 connected to the conductive layer;characterized in that the conductive layer comprises a plurality of orifices 6 filled with an silicone rubber throughout the conductive area.

The term "sensor" as used herein, refers to a component that receives physiological signals and transforms them into electrical signals.

The term "electrode" as used herein, refers to the area of the conductive layer that is in contact with the skin and wherein the physiological signal is received.

The term "track" as used herein, refers to the area of the conductive layer where the electrical connector is located. The track transmitters the physiological signal from the electrode area to the electrical connector.

The term "electrical connector" as used herein, refers to an electromechanical device which provides a separable interface between two electronic subsystems, sensor and electronic instrument, without an unacceptable effect on signal integrity.

The term "anti-slip material" as used herein, refers to a material with a material/skin friction coefficient of al least 0.5. In a preferred embodiment, the anti-slip material is silicone rubber.

The term "hot melt adhesive" as used herein, refers to a thermoplastic, non-structural adhesive that flows when heated and hardens and strengthens as it cools.

The term "screen printing", as commonly known in the art, refers to a process made using a stencil in which image or design is print on a very fine mesh screen and the printable material is squeegeed onto the printing surface through the area of the screen that is not covered by the stencil.

Traditionally the process was called screen printing or silkscreen printing because silk was used in the process. Thus, "silk printing", "screen printing" and "silk screen printing" are synonymous among them.

In an embodiment of the first aspect of the invention, the conductive layer 2 is made of conductive material, selected from conductive fabric.

In another embodiment of the first aspect of the invention, it is provided a sensor 1 adapted to be integrated in a garment 7 so as to be placed in contact with skin 12 of a user during the use of the garment 7, wherein said sensor 1 comprises a conductive layer 2 to be placed in contact with the skin 12 for receiving physiological signals comprising at least:an electrode 3; a track 4; and an electrical connector 5 connected with the track 4; wherein the electrode 3 of the conductive layer 2 comprises a plurality of orificies 6 or grooves 11 in a predefined pattern filled with an anti-slip material. Preferably the electrode 3 of the conductive layer 2 comprises a plurality of orificies.

According to an embodiment of the invention the electrode 3 and the track 4 are made of the same or different material. In a preferred embodiment of the first aspect of the invention the electrode 3 and track 4 independently from each other is a conductive fabric comprising conductive fibers and non conductive fibers.

In a preferred embodiment of the first aspect of the invention, the electrode 3 and the track 4 refer to a conductive fabric made of conductive fibers.

In other preferred embodiment of the first aspect of the invention, the electrode 3 and track 4 refer to a conductive fabric made of conductive fibers and non conductive fibers.

Preferably, the conductive fibers are made of silver coated nylon (such as Xstatic® yarns from Laird Sauquoit Industries) and the non conductive fibers are made of nylon.

Non limiting examples of conductive fibers are fiber made of silver, copper, nickel, stainless steel, gold, non conductive fibers coated with a conductive material or mixtures thereof. Non limiting examples of coating conductive materials are silver, cooper, nickel, stainless steel, gold and silicone rubber loaded with carbon or silver powder.

Non limiting examples of non conductive fibers are wool, silk, cotton, flax, jute, acrylic fiber, polyamide polyester, nylon and/or with elastic yarns (such as LYCRA® branded spandex from Invista™ S.a.r.l).

The conductive layer with conductive and non conductive fibers are not only more flexible than the conductive layer formed from metal fibers only, but also tend to be lighter and more resistant to oxidation. Because the fibers can be knit tightly, the electrical conductivity of the fabric can be maintained despite a partial loss of the conductive coating on particular threads, whereas in metal fiber conductive fabrics, the fabric may lose operability after a break in one of the fibers, particularly if the fibers are spaced far apart. The amount of metal in the fabric is a compromise between the demand to increase the conductivity and the necessity to improve the touch sensation of the cloth.

As a result of the interlacing of fibers, the fabric shows a plurality of orificies 6 among fibers. According to an embodiment of the invention, the electrode is drilled or grooved in order to make additional orificies 6 or grooves 11 or to make larger the orificies 6 of the electrode in a predefined pattern.

The plurality of orificies 6 or grooves 11 present different pattern as circular, sinusoidal pattern, straight lines pattern, hexagon pattern and other different geometric shapes pattern, or a combination thereof. The plurality of orificies 6 form a matrix random or organized.

The presence of such orificies 6 or grooves 11 in the conductive layer results in an improvement of the elasticity of the layer. By filling the conductive layer orificies 6 or grooves 11 with the silicone rubber it is reached an improvement of the adherence of the sensor to the skin and at the same time it is improved the signal measured, because the noise of the signal is reduced.

The silicone rubber before the process of cured is in a liquid state. When the silicone is in the liquid state is printing in the fabric. This means that the union silicone-fabric is an union without an adhesive. The electrically conductive layer described in the invention is integrated into the fabric. The silicone in the liquid state when is printing in the fabric is capable to penetrate in the orificies of the fabric, anchoring with the structure of the conductive layer.

When the orificies 6 or grooves 11 are filled, the silicone rubber present a flat or relief profile. In a preferred embodiment the silicone rubber shows a relief profile.

In a preferred embodiment the silicone rubber is a silicone rubber with molecular weight comprised between 400 g/mol and 600 g/mol.

As described above the sensor 1 of the invention is to be placed in contact with the skin 12. In a preferred embodiment the proportion of conductive layer 2 to be in contact with the skin is comprised between 50% and 80% of the conductive layer and the proportion of the silicone rubber to be in contact with the skin 12 is comprised between 20% and 50% in respect to the total conductive layer 2. In a most preferred embodiment the proportion of conductive layer 2 to be in contact with the skin 12 is comprised between 60% and 70% of the conductive layer 2 and the proportion of the silicone rubber to be in contact with the skin 12 is comprised between 30% and 40% in respect to the total conductive layer 2.

In a preferred embodiment the track 4 and the electric connector 5 are covered with an insulating material 8.

In sensor on contact with the skin of the user the electrode/skin resistance is one of the elements to determine the noise of the signals. In a preferred embodiment the resistance of the electrode 3 is comprised between 1Ω and 10Ω. In a more preferred embodiment the resistance of the track 4 is comprised between 1Ω and 50 kΩ.

A second aspect of the present invention is a device comprising at least one sensor 1 of the invention and an electronic instrument 14 for receiving and collecting and/or storing and/or processing, and/or transmitting data from said sensor.

Using the sensor of the invention, the physiological signals detected can be at least one of the following data: cardiac pulse, respiratory frequency, electrodermal response (EDR), measures electrical skin conductivity, electrocardiography (ECG), electromyography (EMG). These signals refer to electrical signals produced in the body. Preferably the data are ECG data.

A third aspect of the present invention is a garment 7 which integrates the device of the invention.

In an embodiment of the third aspect, the garment 7 is designed for applying a pressure equal or higher than 2 KPa. In another embodiment the garment 7 comprises two layers, an inner and an outer layer 13, and the outer layer 13 compresses the sensor to the body with at least 2 KPa. In a most preferred embodiment the outer layer 13 comprises a system to regulate the pressure.

Preferably, the inner layer has low elasticity and the outer layer 13 has high elasticity. The inner layer is comprised of a blend of synthetic fiber and spandex, wherein the synthetic fiber comprises 85% to 90% by weight of the composite elastic material and most preferably 87% to 89%, and wherein the spandex comprises 10% to 15% by weight of the composite elastic material, and most preferably 11% to 13%. The outer layer 13 is comprised of a blend of synthetic fiber and spandex, wherein the synthetic fiber comprises 92% to 97% by weight of the composite elastic material and most preferably 94% to 96%, and wherein the spandex comprises 3% to 8% by weight of the composite elastic material, and most preferably 4% to 6%. The outer layer 13 compresses the sensor to the skin, and the stability and fixation of the sensor 1 are improved.

In an embodiment of the third aspect, the track 4 of the conductive layer 2 of the sensor 1 is placed between the inner and the outer layer 13 of the garment, and the electrode 3 is over the inner layer of the garment, the electrode 3 being able to be in contact with the skin 12 of the user of the garment 7.

The sensor 1 can be prepared by a process comprising the steps of:
a) die cutting a conductive layer of conductive fabric;
b) adding a hot melt adhesive on one surface of the conductive layer;
c) screen printing with an anti-slip silicone rubber on the the orificies 6 or grooves 11 of the electrode 3, at a temperature comprise between 10-30° C.; and
d) curing the silicone, preferably for up two minutes at a temperature comprised between 130-190° C.

The process can further comprise the step of screen printing with an silicone rubber loaded with an conductive material to form the track 4.

Figure 1B:
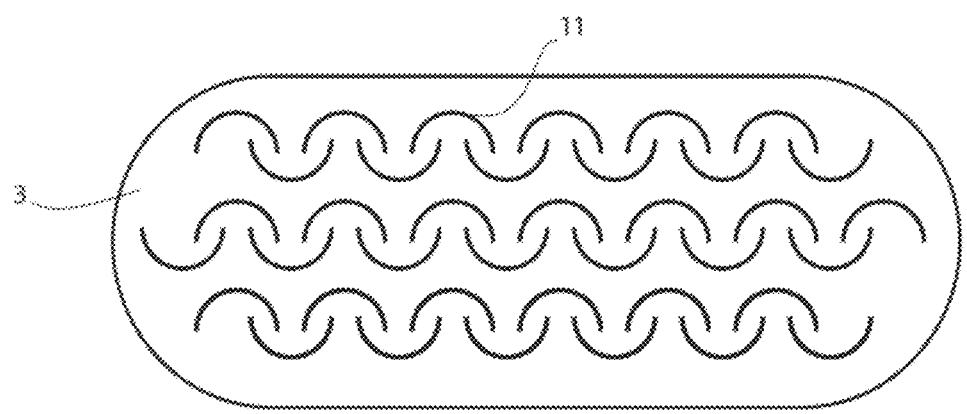
FIG. 1B illustrates a grooves 11 pattern in the electrode 3.
Figure 1C:
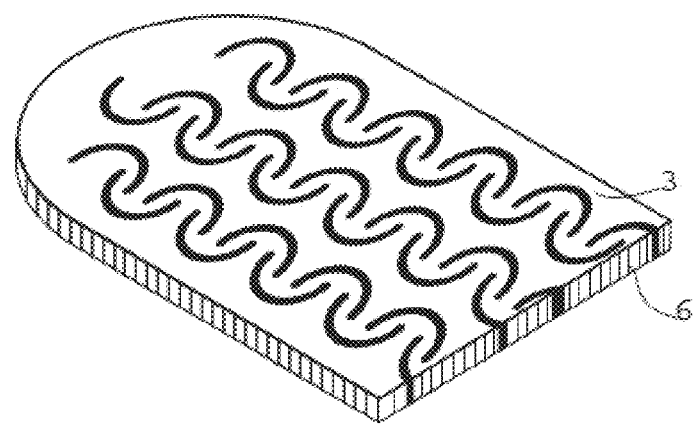
FIG. 1C illustrates an orifices 6 pattern in the electrode 3 with silicone rubber pattern on the surface of the electrode 3.
Figure 1D:
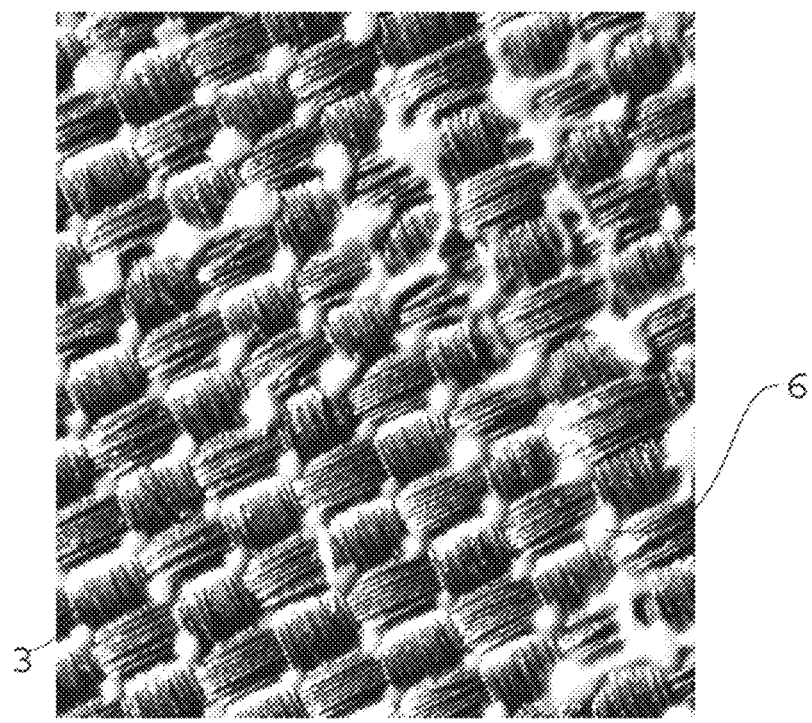
FIG. 1D illustrates a front view of a conductive fabric with the orifices 6 filled with silicone rubber.

A particular embodiment of the invention orifices 6 pattern of the electrode 3 is illustrated in FIG. 1A. FIG. 1B shows a preferred grooves pattern 11 of the electrode 3. FIG. 1C illustrates an electrode 3 with the orifices 6 filled with silicone rubber, wherein the electrode 3 shows the silicone rubber in a predefined pattern on their surface in a relief profile. Therefore, the silicone rubber anchorages with the fabric of the electrode, through the filling of the orifices.

Figure 2:
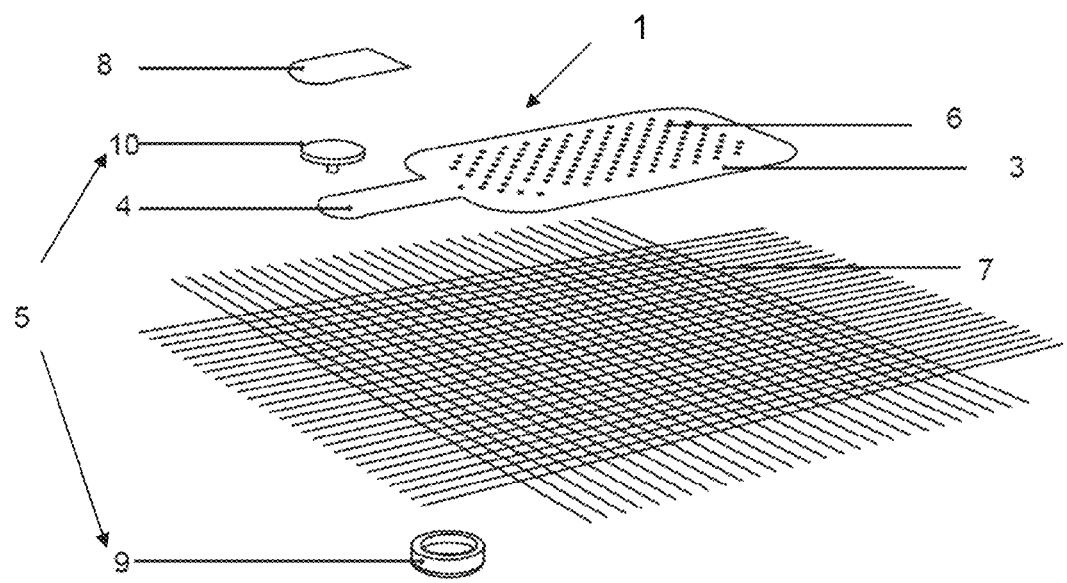
FIG. 2 illustrates an exploited perspective view of an embodiment of a sensor 1 according to the present invention.

FIG. 2 shows an exploited perspective view of a sensor 1 wherein the conductive layer 2 comprises the electrode 3 and track 4. As mentioned above, the electrode 3 present circular orifices 6 filled with silicone rubber. The electrical connector 5 is in contact with the track 4 of the conductive layer 2 and the track 4 can be covered with an insulating material 8. The electrical connector 5 comprises a first and second portion, wherein the first portion comprise a female-type clip portion 9 and the connector second portion may comprise a male-type stud portion 10, which portions mate with each other.

Alternatively, the connector first portion may comprise a male-type stud portion and the connector second portion may comprise a female-type clip portion, which portions mate with each other. Typically, when the sensor 1 is integrated in a garment 7, male a female portions of the electrical connector are placed on the opposite face of the garment each other. Thus, the male or female portion which is placed in the inner face, which will be in contact with the skin 12 of the user, is covered with an insulating material 8, which also covers the track 4 of the conductive layer 2.

Figure 3A:
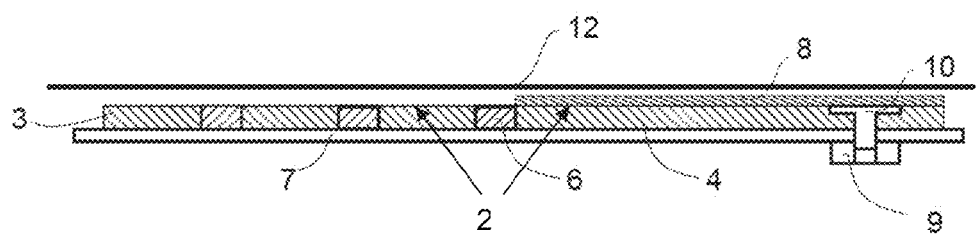
FIG. 3A illustrates a cross-section of an embodiment of a sensor 1 according to the present invention.

FIG. 3A illustrates a cross-section of the sensor 1 of the invention. The cross-section of the sensor 1 shows the electrode area 3 and the circular orifices 6 filled with silicone rubber. The track 4 is made of the same material than the electrode 3. The track and the electrode are made of conductive fabric. The sensor of the invention is in contact with the skin 12.

Figure 3B:
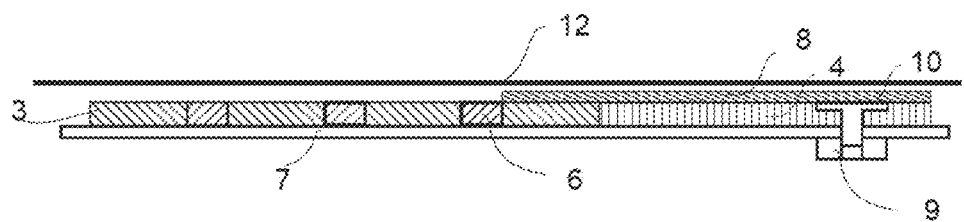
FIG. 3 B illustrates a cross-section of an embodiment of a sensor 1 according to the present invention.

FIG. 3B illustrates a cross-section of an embodiment of a sensor 1 according to the present invention. In this embodiment the electrode is made of conductive fabric and the track 4 is made of silicone rubber loaded with a conductive material.

Figure 4:
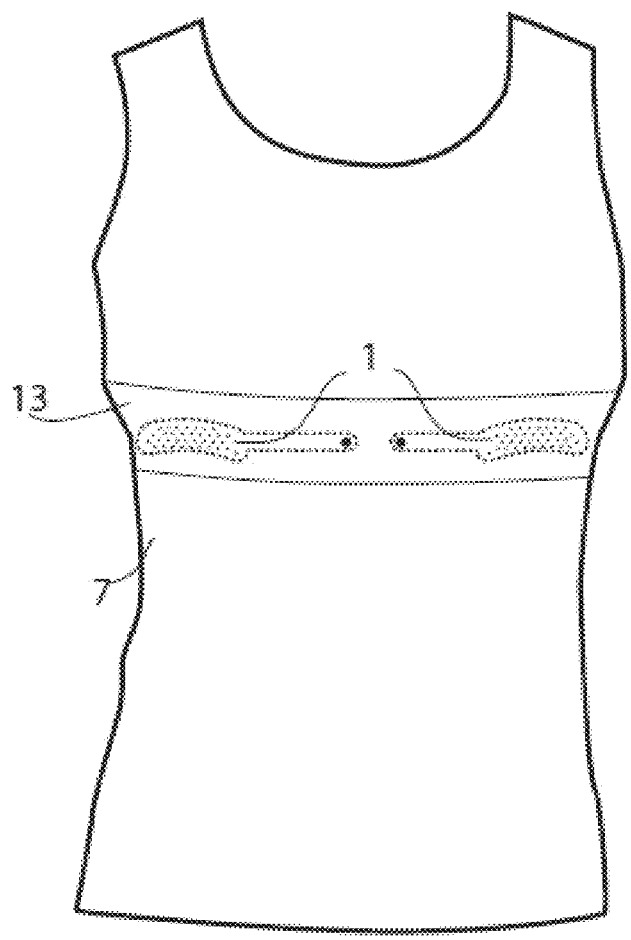
FIG. 4 illustrates an elevation view of the garment 7 according to an embodiment of the present invention.

FIG. 4 illustrates an elevation view of the garment 7 with two sensor 1 placed near the chest area. The outer layer 13 of the garment 7 presses the sensor with at least 2 KPa.

Figure 5:
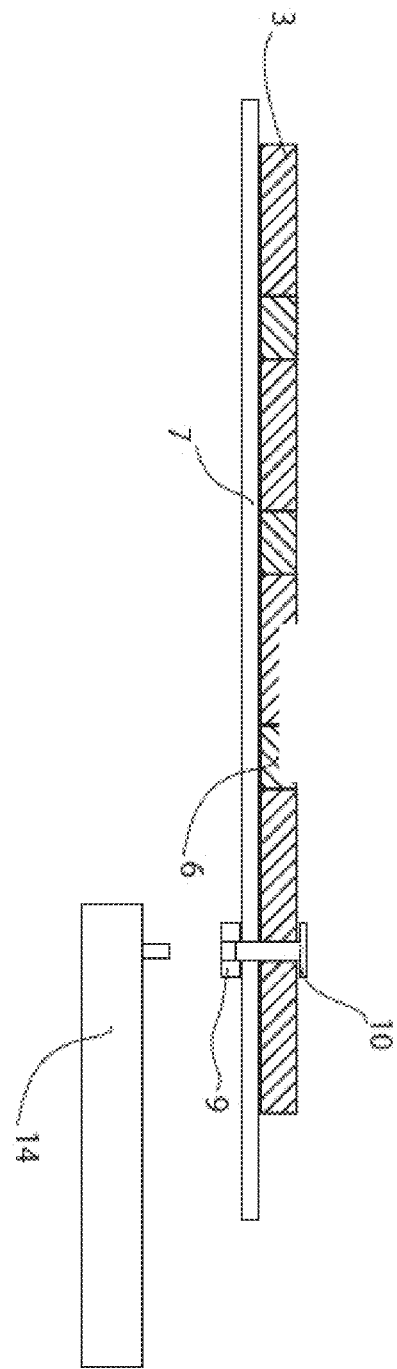
FIG. 5 illustrates a cross-section elevation view of a connection between an embodiment of a sensor 1 according to the present invention and an electronic instrument 14.

FIG. 5 illustrates a cross-section elevation view of a connection between an embodiment of a sensor 1 according to the present invention and an electronic instrument 14. The sensor 1 is connected to the electronically connector 5 using a female-type clip portion 9 and a male-type stud portion 10.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

Comparative Example Between a Garment with the Sensor of the Invention and Other Garments With Fabric Sensor Technology Zephyr™ HxM (made by Zephyr Technology Corporation) (I), Polar TEAM$^2$ (made by Polar Electro, OY.) (II), Numetrex® Cardio-Shirt (made by Textronics, Inc.) (III) and the shirt of the invention (IV), wherein the track and the electrode are made of conductive fabric and the electrode area has the orifices filled with silicone rubber, were tried. The Numetrex® Cardio-Shirt is a shirt with textile electrodes knitted into the fabric. The Zephyr™ HxM strap and Polar TEAM$^2$ strap are straps with textile electrodes. The Zephyr™ HxM strap includes an electrode and a resilient compressible filler provided between the garment and the electrode such that, in use, the electrode is held substantially in place against the skin when the garment moves relative to the user's skin. The Polar TEAM$^2$ strap includes a contact layer including conductive fibres, and a moisture layer for retaining moisture on top of the contact layer.

The test protocol in which performed activities were divided in different levels of physical exigency: resting, daily activity and strong physical activity.

The subject was monitored with a device compatible with all the straps and shirts tested.

The exercises of the protocol were defined as following:
Resting (A): the subject remained lay down in a table for 30 seconds.
Daily activity is defined by:
Stand (B): the subject stood on his feet still for 20 seconds without moving.
Sit down/stand up (C): the subject sat down and stood up of a chair 4 times, remaining 3 seconds in each state.
Bend down (D): the subject bent down 3 times, always in the same way (without flexing his knees).
Arm movement (E): the subject moved his arms in different directions (straight, horizontal and vertical) 3 times each.
Walk (F): The subject walked at a approximate speed of 3 km/h for 20 seconds.

Strong Physical Activity (H) is defined by:

Moderate-speed Running (I): the subject ran at a speed of 6 km/h during 20 seconds.

Fast-speed Running (J): the subject sped up his pace until he reached 10 km/h, then he stayed running at this speed during 15 seconds.

Strong arm movement (racket move) (K): the subject moved his arm strongly simulating hitting a ball with a racket (with both arms), doing this movement 5 times.

Torso turning (L): keeping the feet in the same position, the subject turned his torso in both directions, 5 times each.

Jumping (M): the subject jumped high, he will run two or three meters and then he will jumped again. He repeated this movement 5 times.

Strong physical activity, were more physical demanding than the daily activity. It is also important to underline that the subject sweated during these exercises, so all of the results were in these conditions.

All the exercises done in the resting and daily activities were with the strap or shirt put directly onto the subject (no sweat) and all the strong physical activity was done with the strap or shirt worn by the subject when he was already sweat.

When the different electrocardiographic signals were obtained with each shirt or strap were performed a sort of measures over these signals to evaluate the different technologies.

The measures performed on the signals were (for each exercise of each activity):

Visual Measures

This measure is a direct recognition, just by watching the signal, of the quality of the signal acquired in terms of morphology and beats detected. This visual recognition is also used to identify what beats (QRS complexes) are recognizable as beats and which of them are too noisy to be recognized by a cardiologist. A total of 250 beats were analyzed for resting and Daily Activity and for Strong Physical Activity. A total of 500 beats were analyzed.

Measures Over the Signal

These measures were made on the signal registered in each exercise of each activity session. These measures involve manual and automatic analysis of the recorded signals.

Autocorrelation:

The signal was segmented each 3 seconds with an overlap of 2 seconds between blocks and the autocorrelation was done of each block. This measure follows the next formula:

$$R_x(m) = (1/N - |m|) \sum_{n=0}^{N-1} x_n x_{n+m}$$

where x is a signal of N samples. Then it's normalized regarding to the value of $R_x(0)$. Then we obtain the autocorrelation maximum that it's not the one in $R_{x\,norm}(0)$, because it's sure that we have a maximum in this point because the signal is compared with itself without shift.

This index give us a measure of how much does the signal resemble to a shifted itself (starting from the premise that a heartbeat and the next one are very similar). In this way, values close to 1 show that the signal is very similar to a shifted copy of itself, so it's clean of noise, while low values closet o zero show that the signal is corrupted by noise.

T-P Segment RMS:

The RMS (Root Mean Square) of the T-P segment was calculated in between heartbeats (aprox. 20 segments). This measure was done for each exercise and, averaged, give an estimate of the noise in the signal, particularly in Resting state, because the T-P segment is isoelectric.

These measures were done manually (to select the beginning and end of each segment). In those signals where the T wave was not present (Zephyr™ HxM and Polar TEAM² straps and Numetrex® Cardio-Shirt in Resting and Daily Activity), the segment is defined between two consecutive heartbeats. This value has to be as low as possible but has to be contextualized with the QRS amplitude (see the point RMS/AmplitudeRS).

Maximum T-P Segment:

It measures the maximum peak of noise of the different T-P segments. This value was useful to see if high peaks of noise contaminate our signal.

Maximum Amplitudes:

The amplitudes of the QRS peaks was measured (R peaks and S peaks, to get RS amplitude) for the beats of each exercise. There was not a preferred value but higher values tend to be better to low ones (low ones are more prone to noise).

RMS/AmplitudeRS:

This factor was calculated with the measures explained in the previous points. This index gives us and accurate idea of the noise of the system in the different exercises. It's normalized regarding to the RS Amplitude because each shirt/strap captures a different amount of signals, different amplitudes, so RMS in the T-P segment has to be contextualized to each sensor strap or shirt. For this value, the lower the better.

Of all the index and values obtained, the most important ones are RMS/AmplitudeRS and Autocorrelation because both of them are very good indicators of the noise that contaminate the signals and how recognizable are the heartbeats in the registered signals.

The results were presented divided in three sections: results for Resting and Daily Activity, results for Strong Physical Activity.

Resting and Daily Activity

Figure 6:
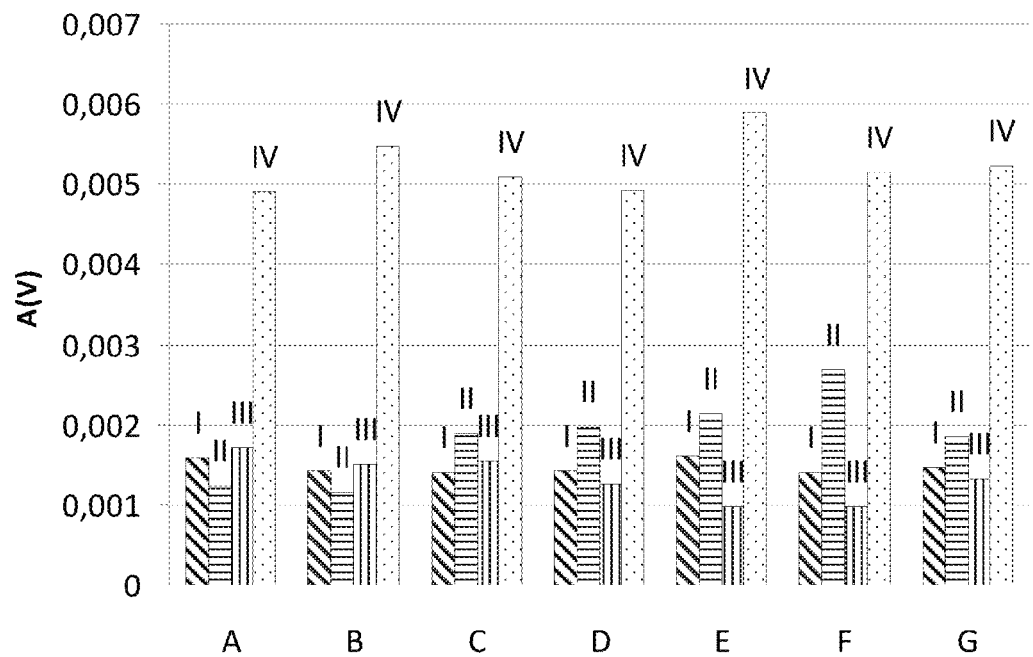
FIG. 6 shows the Amplitude RS (A(v)) in resting (A), stand (B), stand/sit (C), bend (D), arms (E), walk (F), and all the activities, resting, stand stand/sit, bend arms and walk (G) for Zephyr™ HxM strap (I), Polar TEAM$^2$ strap (II), Numetrex® Cardio-Shirt (III) and the shirt of the invention (IV).

FIG. 6 shows the amplitude RS (A(v)) in resting (A), stand (B), stand/sit (C), bend (D), arms (E), walk (F), and all the activities, resting, stand stand/sit, bend arms and walk (G) for Zephyr™ HxM strap (I), Polar TEAM² strap (II), Numetrex® Cardio-Shirt (III) and the shirt of the invention (IV). The amplitude RS gives an idea of how much signal does our system capture, so a high amplitude RS is better. FIG. 6 shows that the shirt of the invention captures better signal than the other systems, it works better in dry conditions (this activity session doesn't involves sweating).

Figure 7:
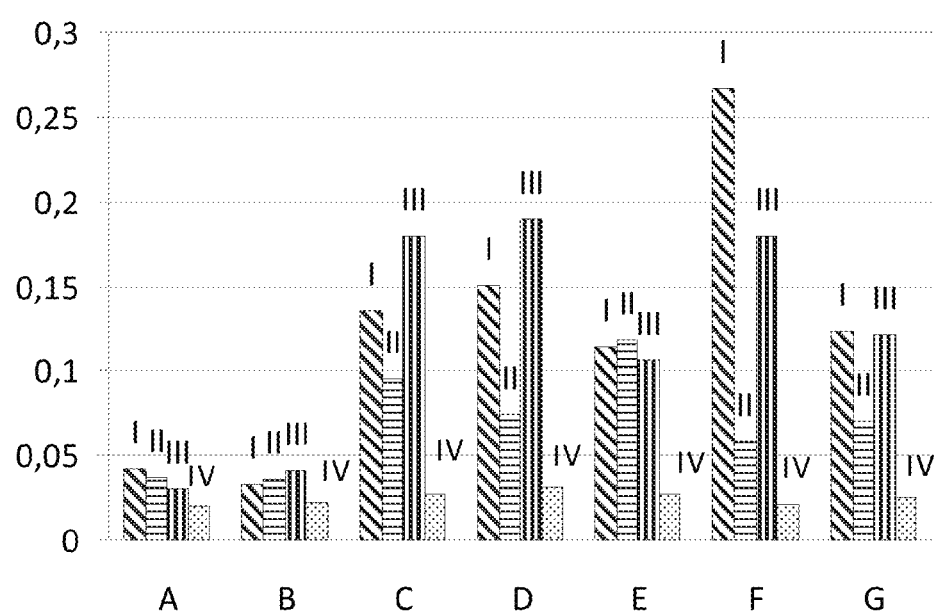
FIG. 7 shows RMS/Amplitude RS in resting (A), stand (B), stand/sit (C), bend (D), arms (E), walk (F), and all the activities, resting, stand stand/sit, bend arms and walk (G) for Zephyr™ HxM strap (I), Polar TEAM$^2$ strap (II), Numetrex® Cardio-Shirt (III) and the shirt of the invention (IV).

FIG. 7 shows RMS/Amplitude RS in resting (A), stand (B), stand/sit (C), bend (D), arms (E), walk (F), and resting and daily activity (resting, stand stand/sit, bend arms and walk) (G) for Zephyr™ HxM strap (I), Polar TEAM² strap (II), Numetrex® Cardio-Shirt (III) and the shirt of the invention (IV).This data is important because the noise is contextualized regarding to the AmplitudeRS, and it's a good measure of the SNR (Signal-to-Noise Ratio) of the system. The value calculated here is Noise-to-Signal, so the lower this value is the better. The shirt of the invention (IV) show the lowest value.

Figure 8:
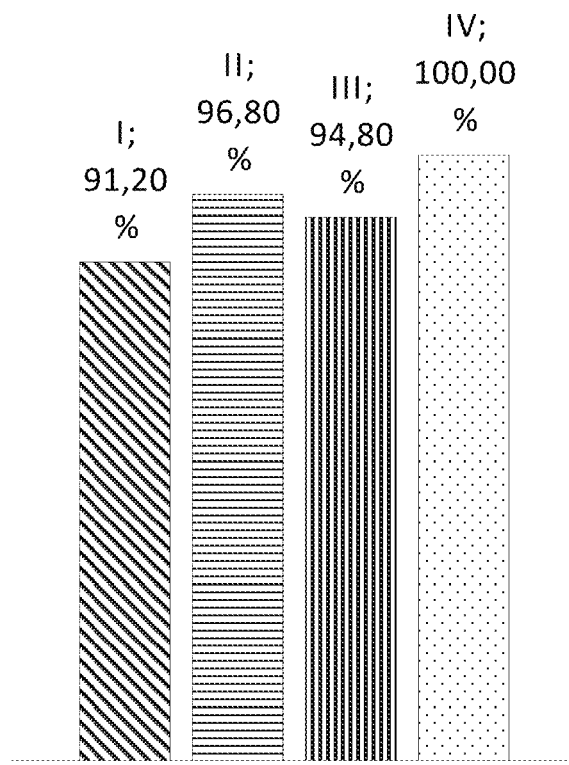
FIG. 8 shows the percentage of good QRS complex in resting and daily activity for Zephyr strap (I), Polar strap (II), Numetrex shirt (III) and the shirt of the invention (IV).

FIG. 8 shows the percentage good QRS complex in resting and daily activity for Zephyr™ HxM strap (I), Polar TEAM² strap (II), Numetrex® Cardio-Shirt (III) and the shirt of the invention (IV). FIG. 8 determines how many beats are recognizable as QRS at first sight. A total of 250 beats were analyzed for each system, and the results here are the total of the Resting and Daily Activity Session (not divided into exercises). The higher the percentage is the better. The highest value it is the value of the shirt of the invention (IV).

Figure 9:
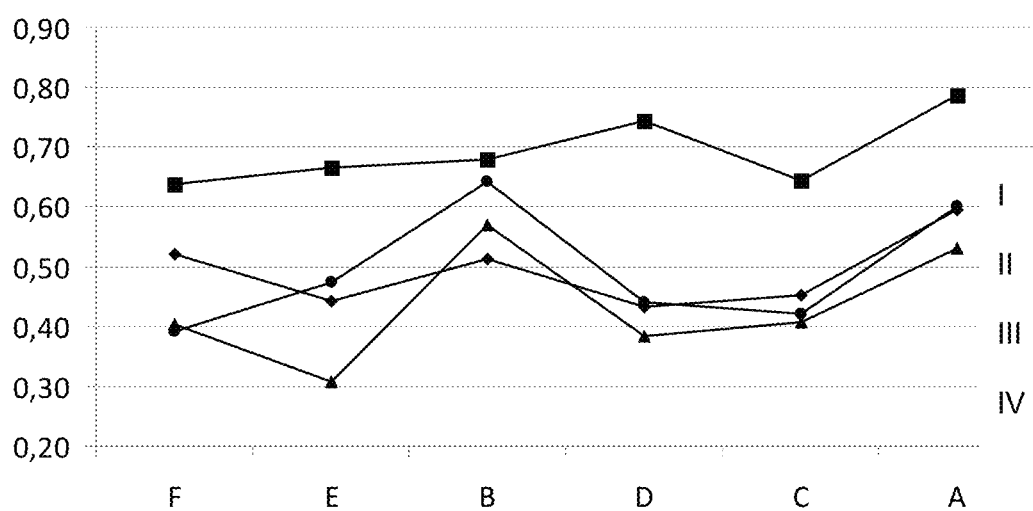
FIG. 9 shows the autocorrelation value for Zephyr™ HxM strap (I), Polar TEAM$^2$ strap (II), Numetrex® Cardio-Shirt (III) and the shirt of the invention (IV),in walking (F), arms(E), stand (B), bend (D), stand/sit (C) and resting (A).

FIG. 9 shows the autocorrelation value for Zephyr™ HxM strap (I), Polar TEAM² strap (II), Numetrex® Cardio-Shirt (III) and the shirt of the invention (IV) in walking (F), arms (E), stand (B), bend (D), stand/sit (C) and resting (A).This information is also important because it is a good indicator of the quality, reproducibility and the similitude between the heartbeats. The closer this value is to 1, the better. The shirt of the invention show the closest value to 1.

Strong Physical Activity

Figure 10:
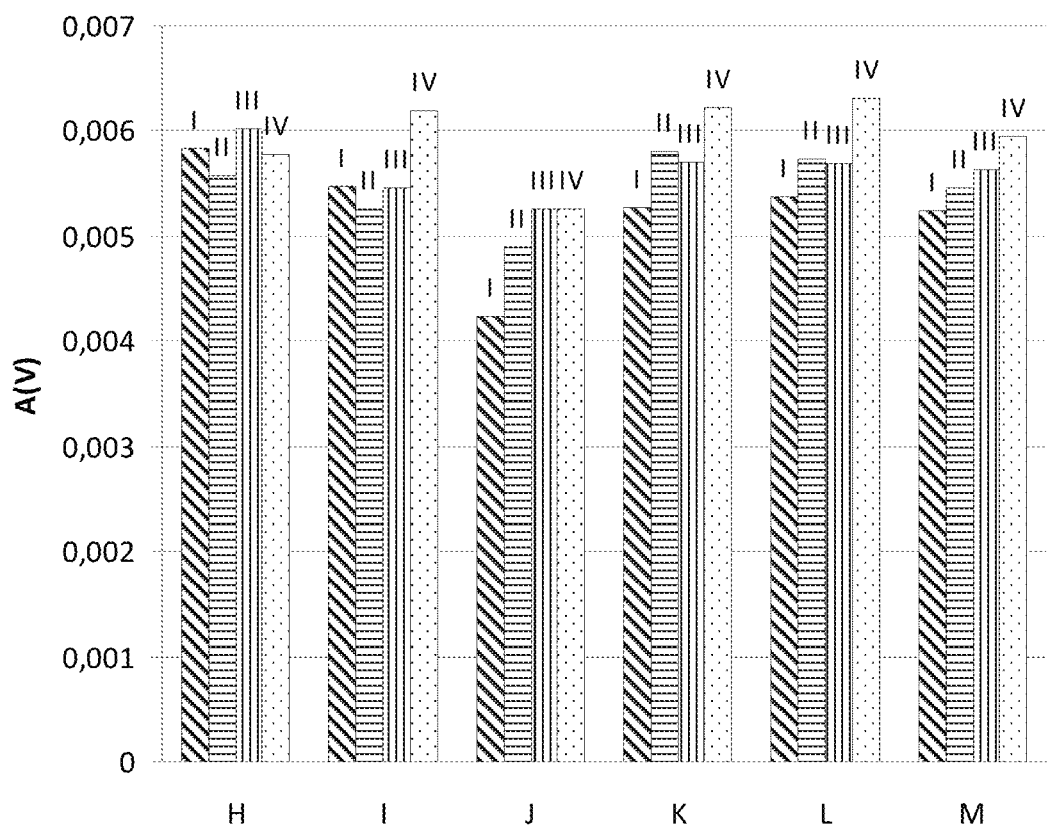
FIG. 10 shows the Amplitude RS (A(v)) in mid-speed (H), fast-speed (I), torso-move (J), racket (K), jump (L), and all the activities, mid-speed, fast-speed, torso move, racket and jump (M) for Zephyr™ HxM strap (I), Polar TEAM$^2$ strap (II), Numetrex® Cardio-Shirt (III) and the shirt of the invention (IV).

FIG. 10 shows the Amplitude RS (A(v)) in mid-speed (H), fast-speed (I), torso-move (J), racket (K), jump (L), and all the activities, (mid-speed, fast-speed, torso move, racket and jump) (M) Zephyr™ HxM strap (I), Polar TEAM² strap (II), Numetrex® Cardio-Shirt (III) and the shirt of the invention (IV). In Strong Physical Activity, due to the sweat, the amplitude of the signal is more similar between technologies, because the sweat helps the conduction of the electric potentials to the electrode and decreases the impedance of the skin-electrode interface.

Figure 11:
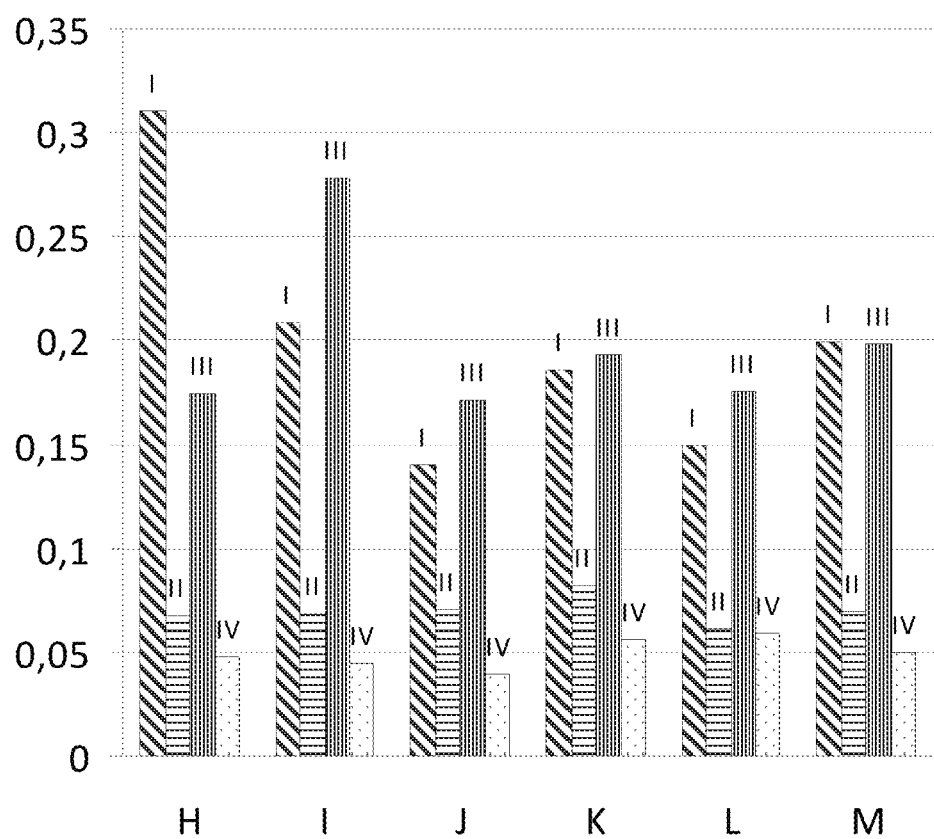
FIG. 11 shows RMS/Amplitude RS in mid-speed (H), fast-speed (I), torso-move (J), racket (K), jump (L), and all the activities, mid-speed, fast-speed, torso move, racket and jump (M) for Zephyr strap (I), Polar strap (II), Numetrex shirt (III) and the shirt of the invention (IV).

FIG. 11 shows RMS/Amplitude RS in mid-speed (H), fast-speed (I), torso-move (J), racket (K), jump (L), and all the activities, mid-speed, fast-speed, torso move, racket and jump (M) for Zephyr™ HxM strap (I), Polar TEAM² strap (II), Numetrex® Cardio-Shirt (III) and the shirt of the invention (IV). Again, we can see here that the shirt of the invention has the best results.

Figure 12:
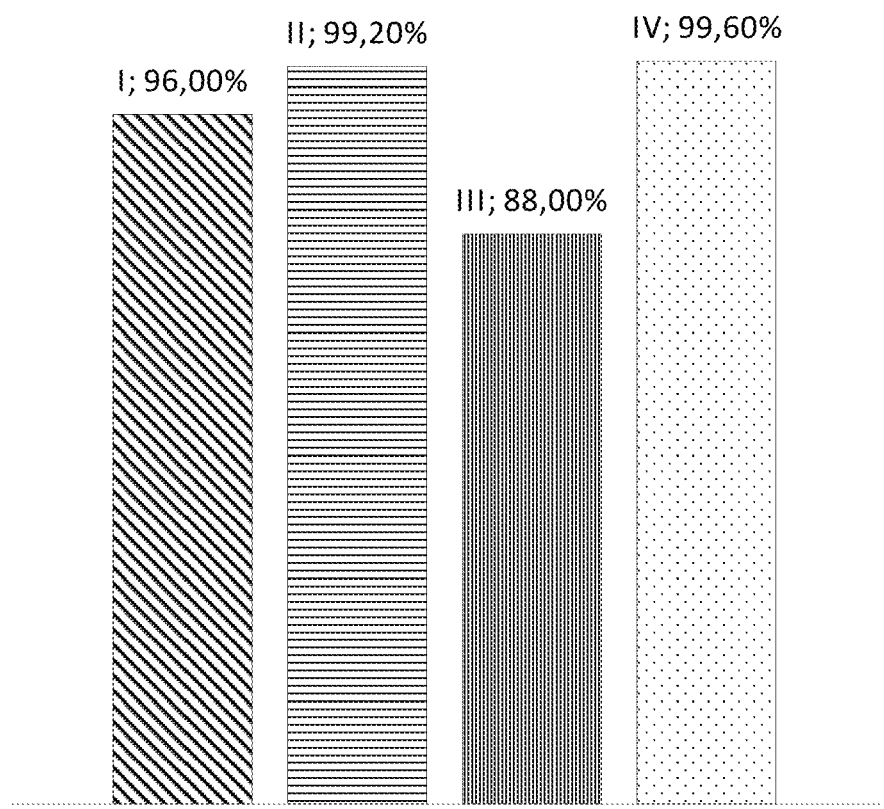
FIG. 12 shows the percentage of good QRS complex in strong physical activity for Zephyr strap (I), Polar strap (II), Numetrex shirt (III) and the shirt of the invention (IV).

FIG. 12 shows the percentage good QRS complex in strong physical activity for Zephyr™ HxM strap (I), Polar TEAM² strap (II), Numetrex® Cardio-Shirt (III) and the shirt of the invention (IV). The shirt of the invention shows the best results.

Figure 13:
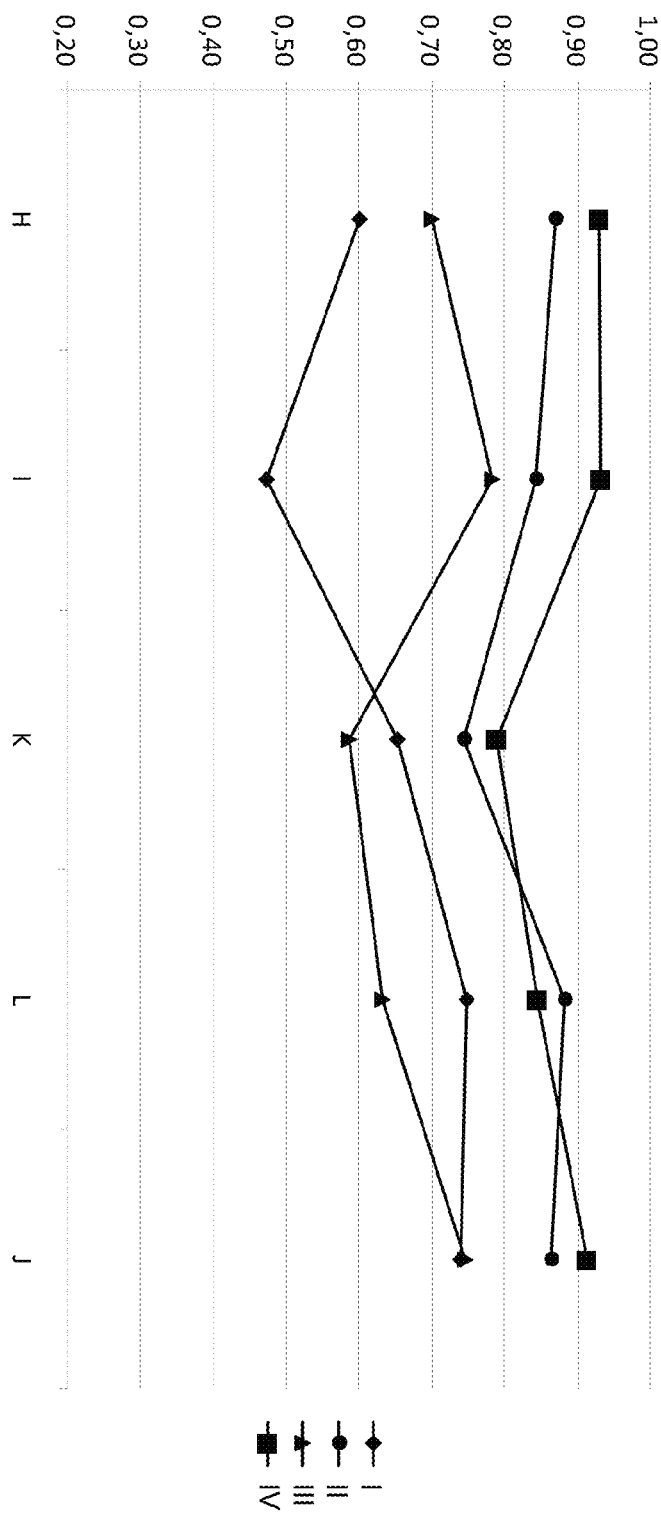
FIG. 13 shows the autocorrelation value Zephyr™ HxM strap (I), Polar TEAM$^2$ strap (II), Numetrex® Cardio-Shirt (III) and the shirt of the invention (IV) in mid-speed (H), fast-speed (I), torso-move (J), racket (K) and jump (L).

FIG. 13 shows the autocorrelation value for Zephyr™ HxM strap (I), Polar TEAM² strap (II), Numetrex® Cardio-Shirt (III) and the shirt of the invention (IV) in mid-speed (H), fast-speed (I), torso-move (J), racket (K) and jump (L). The shirt of the invention shows the best result.

In conclusion the shirt of the invention seems superior when we are in a situation of dry interface skin-electrode (no sweating), giving a much better signal and more stable than the other systems. In a Strong Physical situations, all the systems work better in terms of signal capture thanks to the sweat, but the shirt of the invention is the one that give a more signal recognizable morphology and stable signal and gives the best result in all of the situations and activities.

Comparative Example Between a Garment with the Sensor of the Invention and the Garments with the Sensor of the Invention Where the Orifices of the Electrode Area were Not Filled with Silicone Rubber.

The shirt of the invention (IV), wherein the track and the electrode are made of conductive fabric and the electrode area has the orifices filled with silicone rubber, and the shirt of the invention without silicone rubber (V) were tried.

The protocol followed was the same described above. Significant differences were obtained in strong physical activity.

Figure 14:
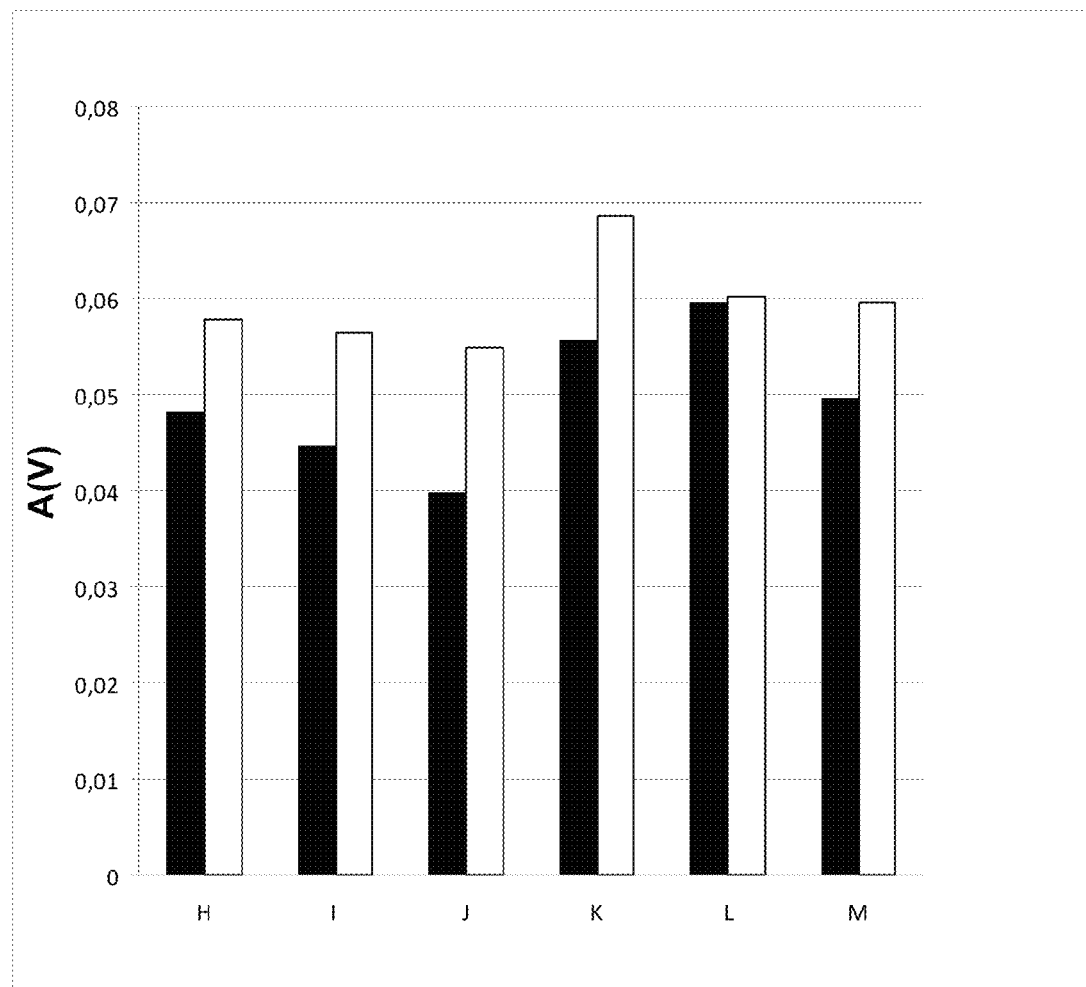
FIG. 14 shows RMS/Amplitude RS in mid-speed (H), fast-speed (I), torso-move (J), racket (K), jump (L), and all the activities, mid-speed, fast-speed, torso move, racket and jump (M) for the shirt of the invention (IV), black column and the shirt of the invention without silicone rubber (V), white column.

FIG. 14 shows RMS/Amplitude RS in mid-speed (H), fast-speed (I), torso-move (J), racket (K), jump (L), and all the activities, mid-speed, fast-speed, torso move, racket and jump (M) for the shirt of the invention (IV) and the shirt of the invention without silicone rubber. The shirt of the invention has the best results, this means less noise and better signal with silicone than without it. The results showed the better adherence to the skin.

The invention claimed is:

1. A sensor for acquiring physiological signals, the sensor comprising:
   a conductive layer comprising a conductive fabric of interlaced conductive and non-conductive fibers and a plurality of orifices throughout the conductive fabric, wherein the plurality of orifices are filled with a silicone rubber, and wherein the silicone rubber is attached to the conductive fabric without the use of an adhesive; and
   an electrical connector connected to the conductive layer, the electrical connector providing a separable interface between the conductive layer and an electronic instrument.

2. The sensor according to claim 1, wherein the conductive layer comprises at least an electrode and a track, the electrical connector being connected to the track.

3. The sensor according to claim 2, wherein the track is covered with an insulating material.

4. The sensor according to claim 1, wherein the conductive fibers comprise 1) fibers including silver, copper, nickel, stainless steel, gold, silicone rubber loaded with carbon or silver powder; 2) non-conductive fibers coated with a conductive material; or 3) a mixture thereof.

5. The sensor according to claim 1, wherein the non-conductive fibers comprise fibers including wool, silk, cotton, flax, jute, acrylic, polyamide polyester, nylon, or elastic yarn.

6. The sensor according to claim 1, wherein the conductive fibers comprise fibers made of silver coated nylon and the non-conductive fibers are made of nylon.

7. The sensor according to claim 1, wherein the silicone rubber is a silicone rubber with molecular weight comprised between 400 g/mol and 600 g/mol.

8. The sensor according to claim 1, wherein the proportion of the conductive layer designed to be in contact with a skin surface comprises between 50% and 80% of the conductive layer and the proportion of the silicone rubber designed to be in contact with the skin surface comprises between 20% and 50% of the conductive layer.

9. A device comprising:
   at least one sensor as defined in claim 1, and
   the electronic instrument for receiving and collecting signals acquired from the at least one sensor.

10. A garment comprising the device as defined in claim 9, wherein the at least one sensor is coupled to the garment so as to be placed in contact with skin of a user during the use of the garment.

11. The garment according to claim 10, wherein a portion of the garment which is coupled to the sensor is designed for applying a pressure equal or higher than 2 kPa.

12. The garment according to claim 10, wherein the garment comprises two layers comprising an inner and an outer layer, and the outer layer is able to compress the sensor to a body of the user with a pressure of at least 2kPa.

13. The garment according to claim 12, wherein the outer layer comprises a system to regulate the pressure.

14. The device of claim 9, wherein the electronic instrument further stores and/or processes and/or transmits data received and collected from the at least one sensor.

15. The sensor according to claim 1, wherein the plurality of orifices form an organized pattern.

16. The sensor according to claim 15, wherein the organized pattern is a circular pattern, sinusoidal pattern, straight line pattern, hexagon pattern, another pattern of geometric shapes, or a combination thereof.

17. The sensor according to claim 1, wherein the silicone rubber is located only in the plurality of orifices.

18. The sensor according to claim 1, wherein the sensor is configured for detecting cardiac pulse, respiratory frequency, electrodermal response, electrical skin conductivity, electrocardiography, and/or electromyography.

19. A process for the preparation of a sensor as defined in claim 1, the process comprising the steps of:
   a) die cutting the conductive fabric;
   b) adding a liquid silicone in a manner that the liquid silicone penetrates and fills the plurality of orifices present in the conductive fabric; and
   c) curing the liquid silicone to form the silicone rubber; wherein steps a) and b) can be carried out in any order.

* * * * *